(12) United States Patent
Choi

(10) Patent No.: US 10,449,304 B2
(45) Date of Patent: Oct. 22, 2019

(54) FLUID INJECTION NEEDLE UNIT HAVING FUNCTION OF PREVENTING NEEDLESTICK INJURY AND INFECTION

(71) Applicant: Keun Uk Choi, Seoul (KR)

(72) Inventor: Keun Uk Choi, Seoul (KR)

(73) Assignee: Jae Won Song (KR)

( * ) Notice: Subject to any disclaimer, the term of this patent is extended or adjusted under 35 U.S.C. 154(b) by 0 days.

(21) Appl. No.: 14/779,361

(22) PCT Filed: Feb. 4, 2015

(86) PCT No.: PCT/KR2015/001124
§ 371 (c)(1),
(2) Date: Sep. 23, 2015

(87) PCT Pub. No.: WO2016/013741
PCT Pub. Date: Jan. 28, 2016

(65) Prior Publication Data
US 2017/0119975 A1    May 4, 2017

Related U.S. Application Data

(63) Continuation of application No. PCT/KR2015/001124, filed on Feb. 4, 2015.

(30) Foreign Application Priority Data

Jul. 21, 2014  (KR) .......................... 10-2014-0091965

(51) Int. Cl.
*A61M 5/32*  (2006.01)
*A61M 5/158*  (2006.01)
(Continued)

(52) U.S. Cl.
CPC .......... *A61M 5/3202* (2013.01); *A61M 5/158* (2013.01); *A61M 5/3273* (2013.01);
(Continued)

(58) Field of Classification Search
CPC .. A61M 5/3202; A61M 5/3273; A61M 5/158; A61M 25/0606; A61M 25/0631;
(Continued)

(56) References Cited

U.S. PATENT DOCUMENTS 6,221,058 B1 * 4/2001 Kao .................. A61M 25/0631
                                                                  604/198
2007/0088278 A1   4/2007  Shue et al.
2013/0085454 A1   4/2013  Song et al.

FOREIGN PATENT DOCUMENTS

EP        1803477 A2      7/2007
KR        20-0391370      8/2005

* cited by examiner

*Primary Examiner* — Imani N Hayman
*Assistant Examiner* — Tiffany Legette
(74) *Attorney, Agent, or Firm* — Park & Associates IP Law, P.C.

(57) ABSTRACT

The present invention relates to a fluid injection needle unit having a function of preventing needlestick injury and infection wherein a cover, a needle body and a body are improved in shape, and after the needle body is inserted into a blood vessel of a patient, the cover is coupled to the bottom end periphery of the body and the needle body is detached from the body by means of detachable mounting members, so that a needle and the needle body are inserted unitarily into the cover to prevent the occurrence of the needlestick injury and infection.

3 Claims, 14 Drawing Sheets

(51) Int. Cl.
*A61M 25/06* (2006.01)
*A61M 5/31* (2006.01)
(52) U.S. Cl.
CPC .... *A61M 25/0606* (2013.01); *A61M 25/0631* (2013.01); *A61M 2005/312* (2013.01)
(58) Field of Classification Search
CPC ........ A61M 25/0693; A61M 2005/312; A61M 2005/3241
USPC ....................................................... 604/192
See application file for complete search history.

FLUID INJECTION NEEDLE UNIT HAVING FUNCTION OF PREVENTING NEEDLESTICK INJURY AND INFECTION

CROSS-REFERENCE TO RELATED APPLICATIONS

The present application is the U.S. National Stage Entry of International Application No. PCT/KR2015/001124, which was filed on Feb. 4, 2015, which claims the benefit of Korean Patent Application No. 10-2014-0091965, which was filed on Jul. 21, 2014, and is hereby incorporated by reference.

BACKGROUND OF THE INVENTION

Field of the Invention

The present invention relates to a fluid injection needle unit having a function of preventing needlestick injury and infection.

Background Information

So as to allow fluids, electrolytes, vitamins, proteins, fats and calories to be maintained and supplied to patients who do not appropriately get essential nutrients through their mouth, to allow the components of blood to be appropriately maintained to them, and further, to allow medicines to be rapidly supplied to them in a state of emergency, generally, the fluids or medicines are injected into their veins through fluid injection needles in hospitals.

So as to inject a given fluid or medicine into the vein of a patient through a fluid injection needle, a needle film for blood vessel injection is first inserted into a blood vessel of the patient, and next, a fluid hose is connected to a hose connector of the needle film.

FIG. 1 is a front view showing a conventional fluid injection needle unit, and FIG. 2 is a front view showing the conventional fluid injection needle unit from which a cover is detached. Further, FIG. 3 is an exemplary view showing the detached state of a needle film from the conventional fluid injection needle unit after the conventional fluid injection needle unit has been inserted into a patient, and FIG. 4 is a front view showing the conventional fluid injection needle unit from which the needle film is detached.

As shown in FIG. 1, a conventional fluid injection needle unit 1 includes a cover 10, a needle film 20, a needle 31, and a body 40. Before the needle film 20 is inserted into the blood vessel of the patient, the cover 10 is mounted on the top end periphery of the body 40.

Further, as shown in FIG. 2, the cover 10 is detached from the body 40 so as to insert the needle film 20 into the blood vessel of the patient, and next, as shown in FIG. 3, the needle 31 and the needle film 20 as a unitary body are inserted into the blood vessel of the patient. After that, only the needle film 20 remains in the state of being inserted into the blood vessel of the patient, while the fluid injection needle unit 1 is pulling out from the blood vessel of the patient.

If the needle film 20 is detached from the conventional fluid injection needle unit 1, as shown in FIG. 4, the needle 31 is exposed to the outside to cause needlestick injury. Accordingly, there is a need to develop a new fluid injection needle unit capable of basically preventing the occurrence of the needlestick injury and infection before and after the needle film 20 is inserted into the blood vessel of the patient.

SUMMARY OF THE INVENTION

Accordingly, the present invention has been made in view of the above-mentioned problems occurring in the prior art, and it is an object of the present invention to provide a fluid injection needle unit having a function of preventing needlestick injury and infection wherein a cover, a needle body and a body are improved in shape, and after the needle body is inserted into a blood vessel of a patient, the cover is coupled to the bottom end periphery of the body and the needle body is detached from the body by means of detachable mounting members, so that a needle and the needle body are inserted unitarily into the cover to prevent the occurrence of the needlestick injury and infection.

To accomplish the above-mentioned object, according to a first aspect of the present invention, there is provided a fluid injection needle unit having a function of preventing needlestick injury and infection, including: a needle film adapted to be inserted into a blood vessel of a patient and having an injection hole formed along the interior thereof; a body having an insertion hole formed to pass through the top and bottom thereof, a top end locking projection formed along the outer top end periphery thereof, and a bottom end locking projection formed along the outer bottom end periphery thereof; a needle body fixed to the insertion hole of the body by means of detachable mounting members before the needle film is inserted into the blood vessel of the patient and detached from the insertion hole of the body after the needle film is inserted into the blood vessel of the patient; a needle fixedly protruding from the top of the body in such a manner as to be inserted into the injection hole of the needle film before the needle film is inserted into the blood vessel of the patient; and a cover having an internal space closed on top thereof and open on bottom thereof and fixedly mounted onto the top end locking projection of the body before the needle film is inserted into the blood vessel of the patient and fixedly mounted onto the bottom end locking projection of the body after the needle film is inserted into the blood vessel of the patient.

According to the present invention, preferably, so as to allow the needle film to be inserted into the blood vessel of the patient, the needle and the needle film are inserted into the blood vessel of the patient after the cover is detached from the body, the needle film is detached from the needle in the state of being inserted into the blood vessel of the patient, the cover is fixedly mounted onto the bottom end locking projection of the body, and the needle body is detached from the body by means of the detachable mounting members, so that the needle body and the needle are accommodated into the cover.

According to the present invention, preferably, the detachable mounting members include a mounting protrusion formed along the outer peripheral surface of the needle body and a locking groove formed along the inner peripheral surface of the insertion hole of the body.

To accomplish the above-mentioned object, according to a second aspect of the present invention, there is provided a fluid injection needle unit having a function of preventing needlestick injury and infection, including: a needle film adapted to be inserted into a blood vessel of a patient and having an expanded tube formed on the lower end periphery thereof and an injection hole formed along the interior thereof; a body having an insertion hole formed to pass through the top and bottom thereof, a top end locking projection formed along the outer top end periphery thereof, a bottom end locking projection formed along the outer bottom end periphery thereof, and an insertion member formed on top thereof; a needle body inserted into the insertion member of the body and fixed thereto by means of the expanded tube of the needle film before the needle film is inserted into the blood vessel of the patient and detached from the insertion member of the body after the needle film is inserted into the blood vessel of the patient; a needle fixedly protruding from the top of the body in such a manner as to be inserted into the injection hole of the needle film before the needle film is inserted into the blood vessel of the patient; and a cover having an internal space closed on top thereof and open on bottom thereof and fixedly mounted onto the top end locking projection of the body before the needle film is inserted into the blood vessel of the patient and fixedly mounted onto the bottom end locking projection of the body after the needle film is inserted into the blood vessel of the patient.

According to the present invention, preferably, so as to allow the needle film to be inserted into the blood vessel of the patient, the needle and the needle film are inserted into the blood vessel of the patient after the cover is detached from the body, the needle film is detached from the needle in the state of being inserted into the blood vessel of the patient, the cover is fixedly mounted onto the bottom end locking projection of the body, and the needle body is detached from the insertion member by means of the detaching of the needle film, so that the needle body and the needle are accommodated into the cover.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF AN ILLUSTRATIVE EMBODIMENT

Hereinafter, an explanation on the configuration and function of a fluid injection needle unit having a function of preventing needlestick injury and infection according to preferred embodiments of the present invention will be in detail given with reference to the attached drawing. According to the present invention, a fluid injection needle unit having a function of preventing needlestick injury and infection is configured wherein a cover is fixedly fitted to the bottom end periphery of a body so as to prevent the needlestick injuries and infection occurring in the conventional fluid injection needle, and after a needle film is inserted into a blood vessel of a patient and thus detached from the needle unit, the needle and a needle body are inserted unitarily into the cover.

Figure 1:
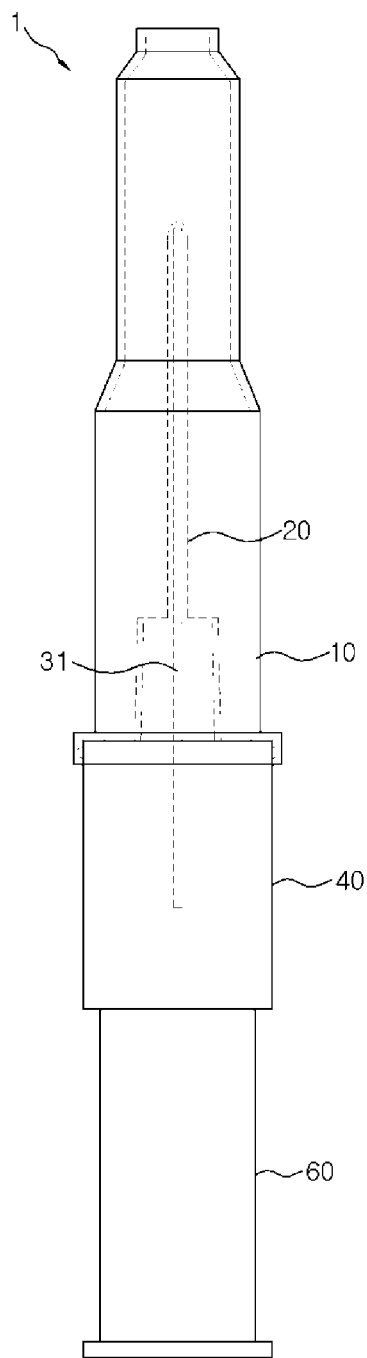
FIG. 1 is a front view showing a conventional fluid injection needle unit.
Figure 2:
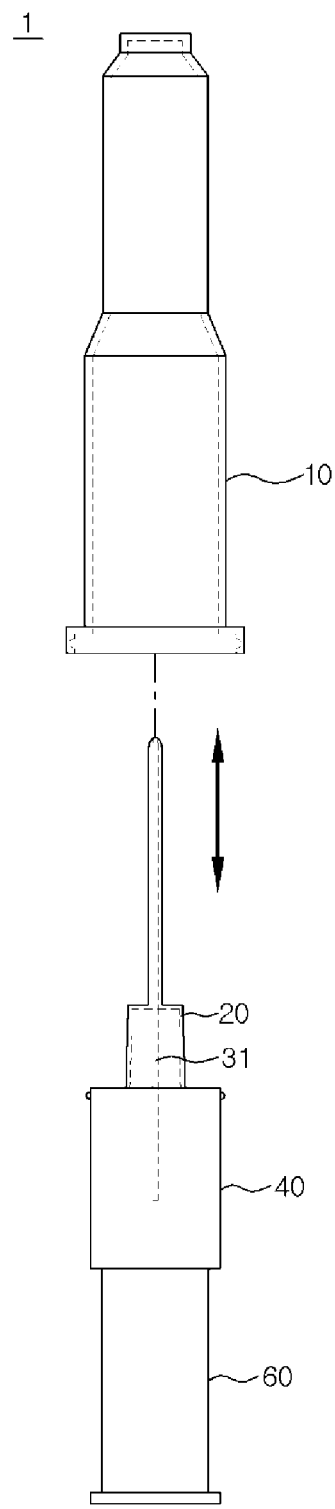
FIG. 2 is a front view showing the conventional fluid injection needle unit from which a cover is detached.
Figure 3:
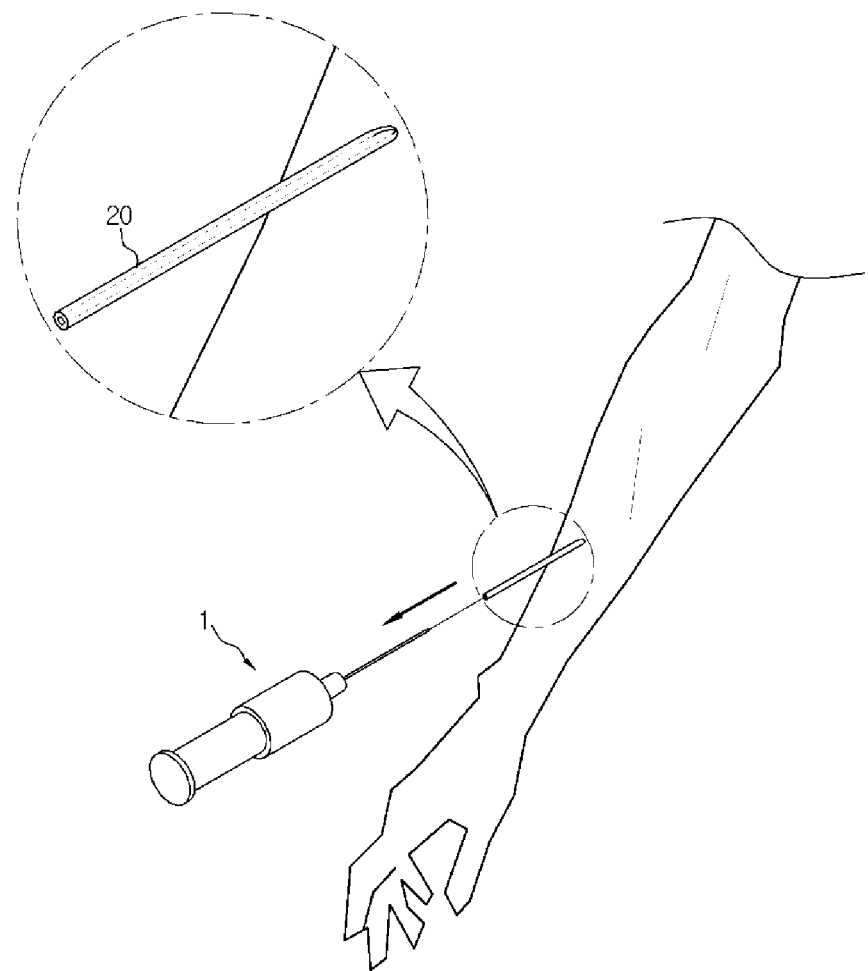
FIG. 3 is an exemplary view showing the detached state of a needle film from the conventional fluid injection needle unit after the conventional fluid injection needle unit is inserted into a blood vessel of a patient.
Figure 4:
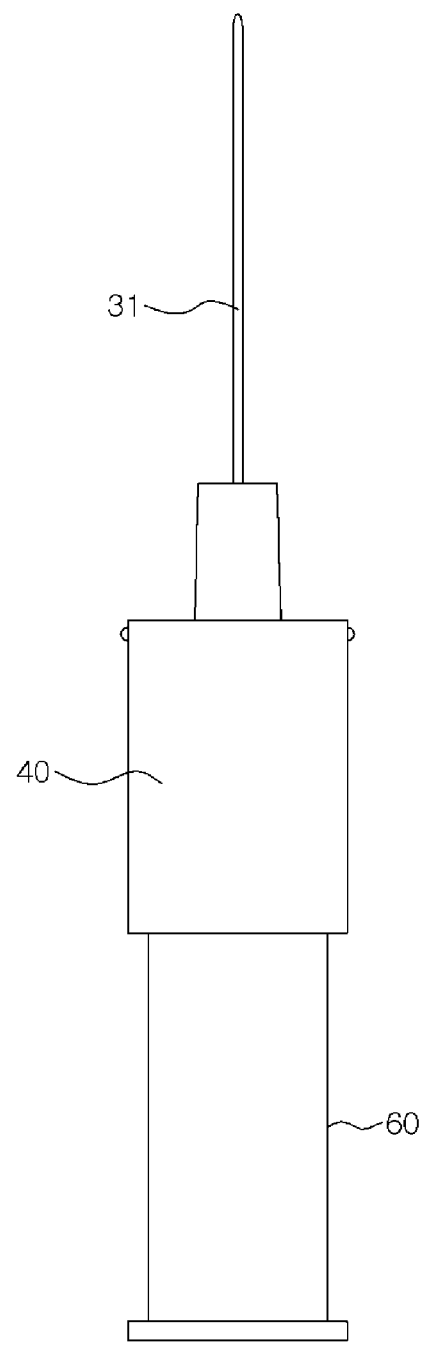
FIG. 4 is a front view showing the conventional fluid injection needle unit from which the needle film is detached.
Figure 5:
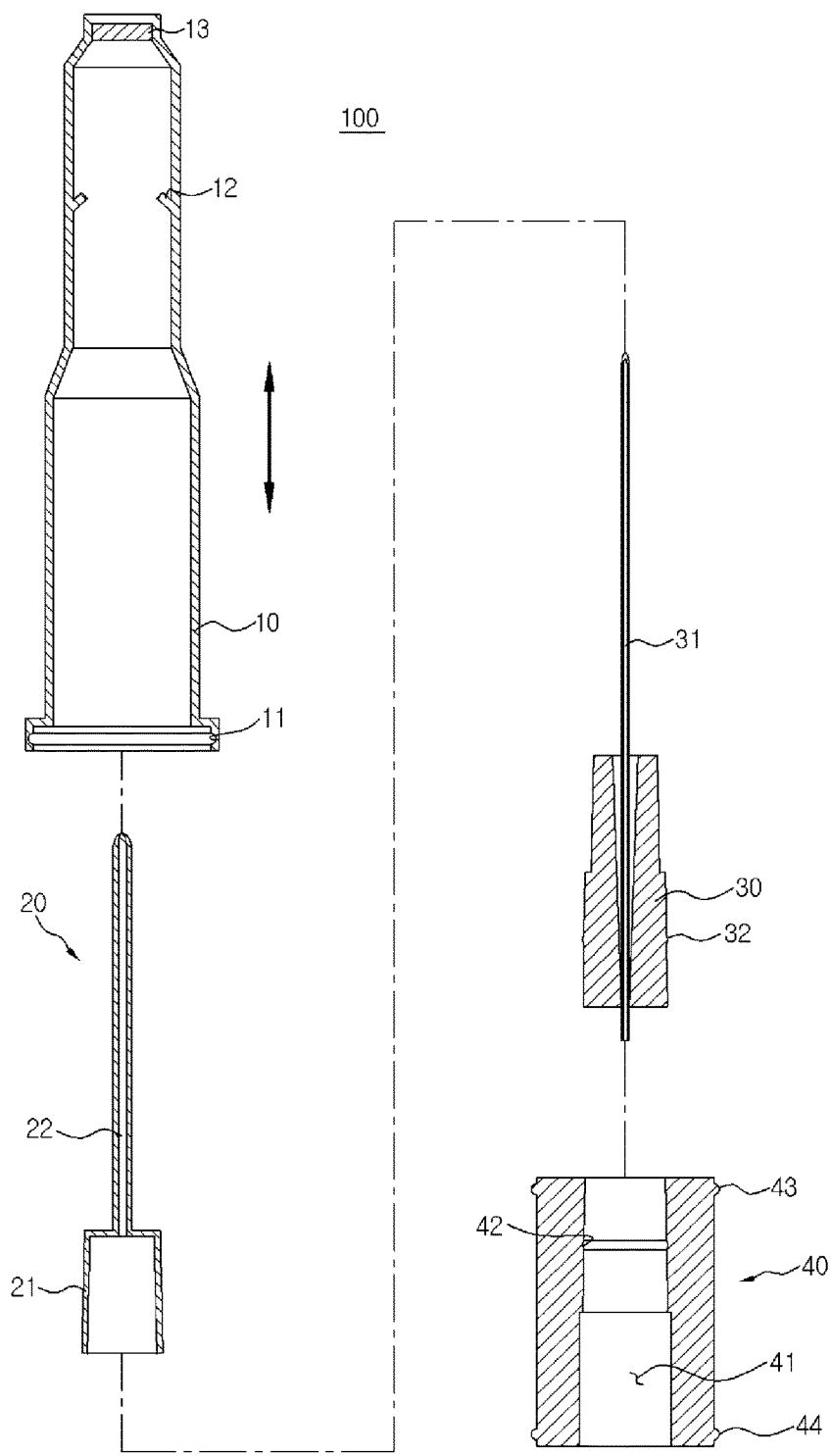
FIG. 5 is an exploded perspective view showing a fluid injection needle unit having a function of preventing needlestick injury and infection according to a first embodiment of the present invention.

Now, an explanation on the configuration and function of a fluid injection needle unit having a function of preventing needlestick injury and infection according to a first embodiment of the present invention will be in detail given with reference to the attached drawing. FIG. 5 is an exploded perspective view showing a fluid injection needle unit having a function of preventing needlestick injury and infection according to the first embodiment of the present invention, and FIG. 6 is a sectional view showing the fluid injection needle unit according to the first embodiment of the present invention.

Figure 6:
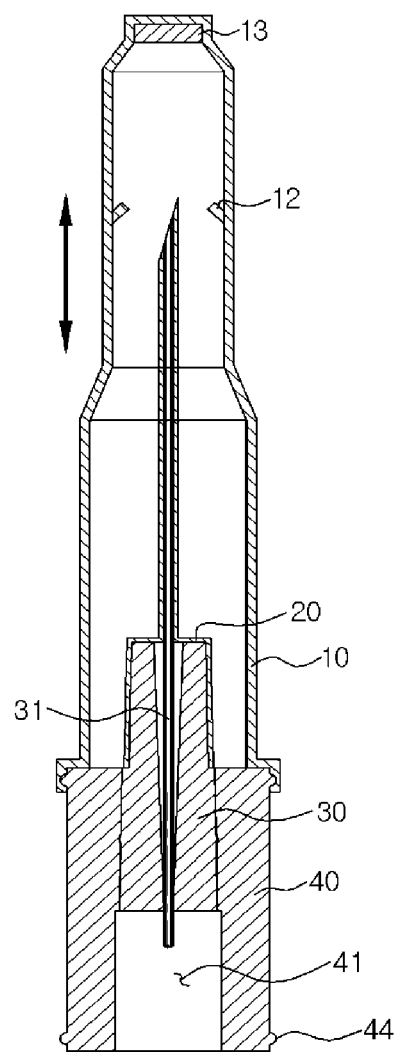
FIG. 6 is a sectional view showing the fluid injection needle unit according to the first embodiment of the present invention.

As shown in FIGS. 5 and 6, a fluid injection needle unit 100 having a function of preventing needlestick injury and infection according to the first embodiment of the present invention includes a cover 10, a needle film 20, a needle 31, a needle body 30, and a body 40.

According to the first embodiment of the present invention, as shown in FIG. 5, the cover 10 is closed on top thereof and open on bottom thereof and has a hollow hole formed at the inside thereof, so that before the needle film 20 is inserted into a blood vessel of a patient, the needle film 20 and the needle 31 are accommodated into the hollow hole of the cover 10, thus preventing the occurrence of the needlestick injury and infection. After the needle film 20 is inserted into the blood vessel of the patient and thus detached from the needle unit 100, accordingly, the cover 10 is mounted onto a bottom end locking projection 44 of the body 40 as will be discussed later in the state of allowing the needle 31 and the needle body 30 to be accommodated thereinto, thus preventing the occurrence of the needlestick injury and infection.

As shown in FIGS. 5 and 6, the cover 10 has a mounting groove 11 formed along the inner bottom end periphery thereof, so that it is mounted onto a top end locking projection 43 formed along the outer top end periphery of the body 40 in a circumferential direction. After the needle film 20 is inserted into the blood vessel of the patient and thus detached from the needle unit 100, the cover 10 is mounted onto the bottom end locking projection 44 formed along the outer bottom end periphery of the body 40 in a circumferential direction.

According to the first embodiment of the present invention, further, the cover 10 includes an absorption layer 13 formed on the inner surface of the closed top end thereof so as to absorb the blood flowing when the needle film 20 is inserted into the blood vessel of the patient and to prevent the occurrence of infection. Furthermore, the cover 10 includes a deviation prevention barrier 12 formed along the inner intermediate periphery thereof so as to prevent the needle 31 and the needle body 30 from being deviated from the interior of the cover 10 when the needle 31 and the needle body 30 after used are inserted into the cover 10 so as to prevent the occurrence of the needlestick injury and infection.

According to the first embodiment of the present invention, further, the needle film 20 is configured to have the needle 31 inserted thereinto, like a general needle film, and after the needle 31 and the needle film 20 are inserted into the blood vessel of the patient, only the needle film 20 is detached from the needle unit 100. The needle film 20 has an expanded tube 21 formed on the lower end periphery thereof and an injection hole 22 formed along the interior thereof. Accordingly, the expanded tube 21 is fitted to the outer upper end periphery of the needle body 30 before the needle film 20 is inserted into the blood vessel of the patient, and after the needle film 20 has been inserted into the blood vessel of the patient, a fluid injection hose (not shown) is insertedly mounted into the expanded tube 21 of the needle film 20.

According to the first embodiment of the present invention, as shown in FIGS. 5 and 6, the needle body 30 has the needle 31 insertedly fixed to the upper end portion thereof and a mounting protrusion 32 formed along the outer peripheral surface thereof. The needle body 30 is desirably made of an elastic material. According to the first embodiment of the present invention, further, the needle body 30 is insertedly mounted on an insertion hole 41 of the body 40 in such a manner as to allow the mounting protrusion 32 to be fixedly mounted on a locking groove 42 formed along the inner peripheral surface of the insertion hole 41 of the body 40. Also, if a given force generated from a user is applied downward from the top end surface of the needle body 30 made of the elastic material to the bottom end surface thereof, the mounting protrusion 32 is released from the locking groove 42 and thus moved down.

According to the first embodiment of the present invention, as shown in FIGS. 5 and 6, the body 40 has the top end locking projection 43 formed along the outer top end periphery thereof, the bottom end locking projection 44 formed along the outer bottom end periphery thereof, and the insertion hole 41 formed to pass through the interior thereof. In the state where the needle film 20 is kept before inserted into the blood vessel of the patient, accordingly, the mounting groove 11 of the cover 10 is fixedly mounted on the top end locking projection 43 of the body 40, and after the needle film 20 is inserted into the blood vessel of the patient and thus detached from the needle unit 100, the mounting groove 11 of the cover 10 is fixedly mounted on the bottom end locking projection 44 of the body 40. Further, the needle body 30 is insertedly fixed to the insertion hole 41 of the body 40.

Next, an operating method of the fluid injection needle unit 100 having a function of preventing needlestick injury and infection according to the first embodiment of the present invention will be explained. As shown in FIG. 6, the needle body 30 is insertedly fixed to the insertion hole 41 of the body 40 in the state where the needle film 20 is kept before inserted into the blood vessel of the patient, and the mounting groove 11 of the cover 10 is fixedly mounted on the top end locking projection 43 of the body 40 in the state where the needle film 20 is fitted to the needle 31, so that the needlestick injury and infection from the needle 31 and the needle film 20 can be prevented.

Figure 7:
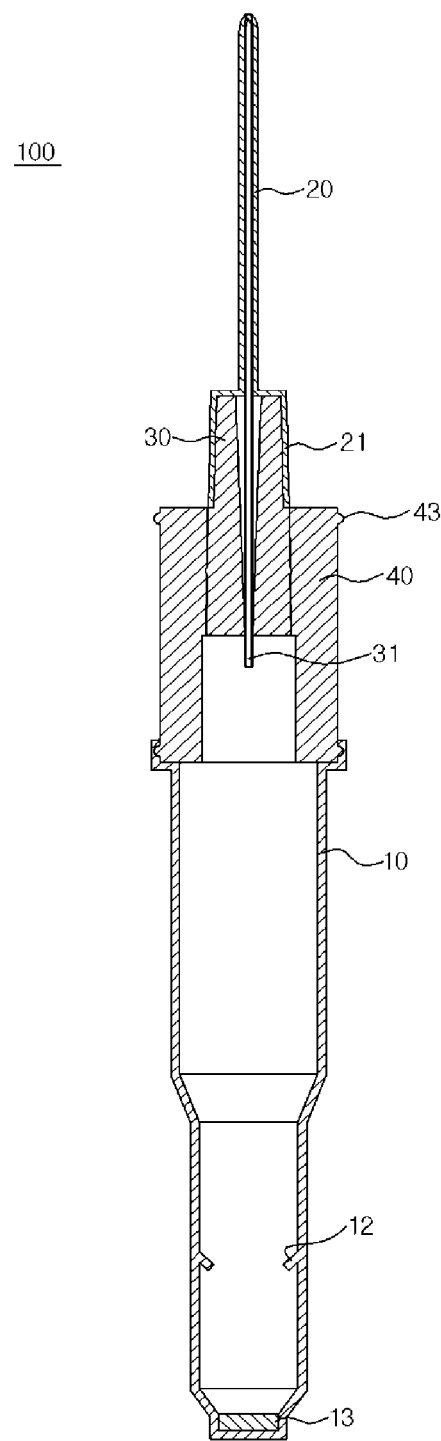
FIG. 7 is a sectional view showing the fluid injection needle unit according to the first embodiment of the present invention, wherein a cover is detached.

So as to allow the needle film 20 to be inserted into the blood vessel of the patient, first, the cover 10 is detached from the body 40. FIG. 7 is a sectional view showing the fluid injection needle unit according to the first embodiment of the present invention, wherein the cover 10 is detached from the top end locking projection 43 of the body 40 and then fixed to the bottom end locking projection 44 of the body 40.

So as to allow the needle film 20 of the fluid injection needle unit 100 to be inserted into the blood vessel of the patient, as shown in FIG. 7, the cover 10, which is mounted onto the top end locking projection 43 of the body 40, is first detached therefrom and then fixed to the bottom end locking projection 44 of the body 40. Next, the needle 31 and the needle film 20 are inserted into the blood vessel of the patient, and after that, only the needle film 20 remains in the state of being inserted into the blood vessel of the patient, while the fluid injection needle unit 100 is pulling out from the blood vessel of the patient.

Figure 8:
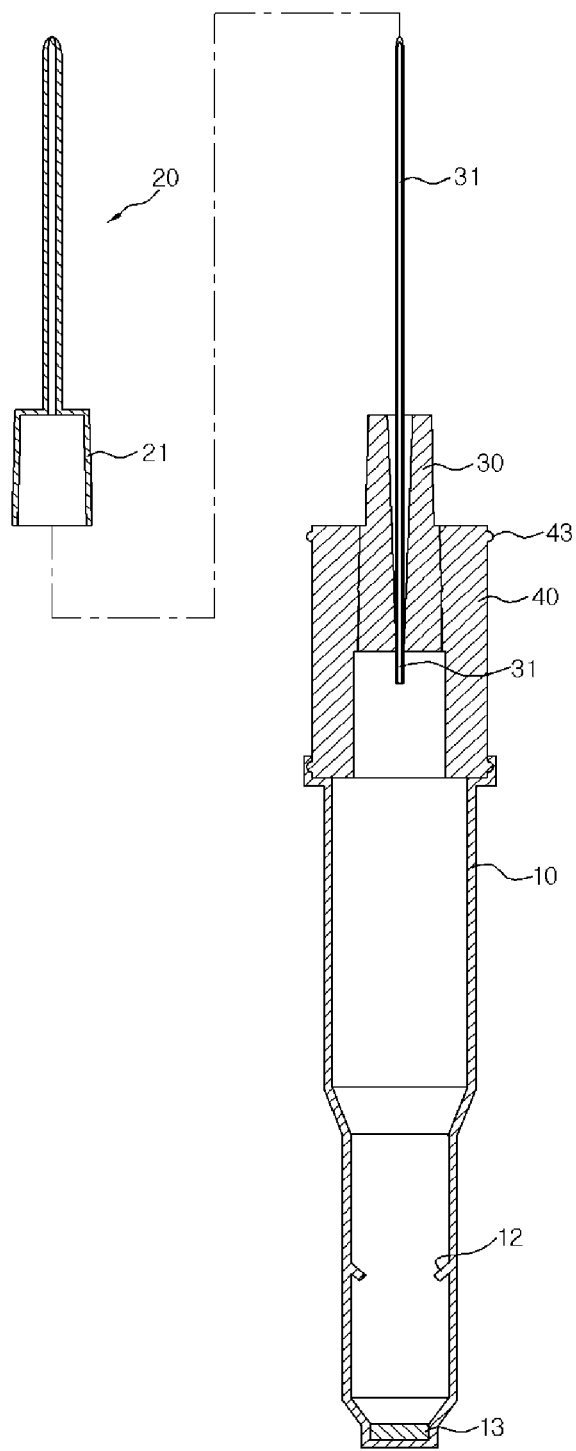
FIG. 8 is a sectional view showing the fluid injection needle unit according to the first embodiment of the present invention, wherein a needle film is detached.

FIG. 8 is a sectional view showing the fluid injection needle unit according to the first embodiment of the present invention, wherein the needle film 20 is detached. That is, FIG. 8 is a sectional view showing the fluid injection needle unit according to the first embodiment of the present invention, wherein the needle film 20 is inserted into the blood vessel of the patient and thus detached from the fluid injection needle unit 100.

According to the first embodiment of the present invention, so as to prevent the occurrence of the needlestick injury and infection after the needle film 20 is detached from the fluid injection needle unit 100, that is, after the fluid injection needle unit 100 is used, the cover 10 is fixedly mounted on the bottom end locking projection 44 of the body 40, and next, the needle body 30 and the needle 31 are unitarily pressed downward and moved to the lower end portion of the body 40.

Figure 9:
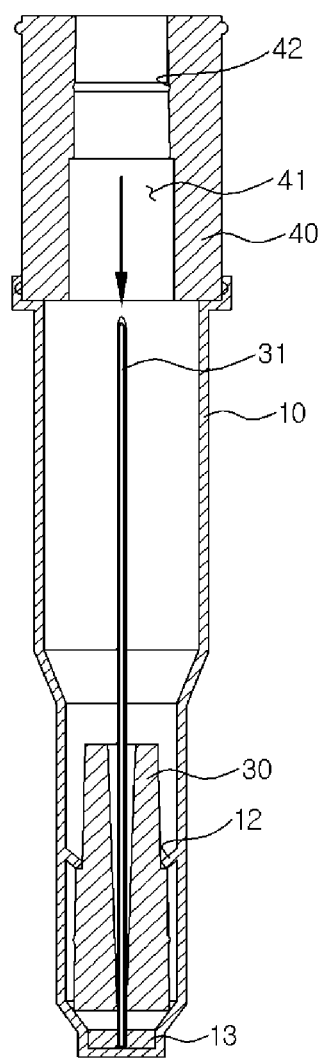
FIG. 9 is a sectional view showing the fluid injection needle unit according to the first embodiment of the present invention, wherein a needle and a needle body are inserted into a cover mounted on the bottom end periphery of a body.

FIG. 9 is a sectional view showing the fluid injection needle unit according to the first embodiment of the present invention, wherein the needle 31 and the needle body 30 are inserted into the cover 10 mounted on the bottom end periphery of the body 40.

According to the first embodiment of the present invention, as shown in FIG. 9, after the needle film 20 of the fluid injection needle unit 100 has been inserted into the blood vessel of the patient, the needle body 30 is moved to the lower end portion of the body 40 by a given force of a user so as to prevent the occurrence of the needlestick injury and infection, and accordingly, the mounting protrusion 32 of the needle body 30 is detached from the locking groove 42 formed on the insertion hole 41 of the body 40, so that the needle body 30 and the needle 31 unitarily drop down, and they are then inserted into the cover 10.

After the fluid injection needle unit 100 is used, accordingly, the needle body 30 and the needle 31 are inserted into the cover 10 mounted on the bottom end periphery of the body 40.

Figure 10:
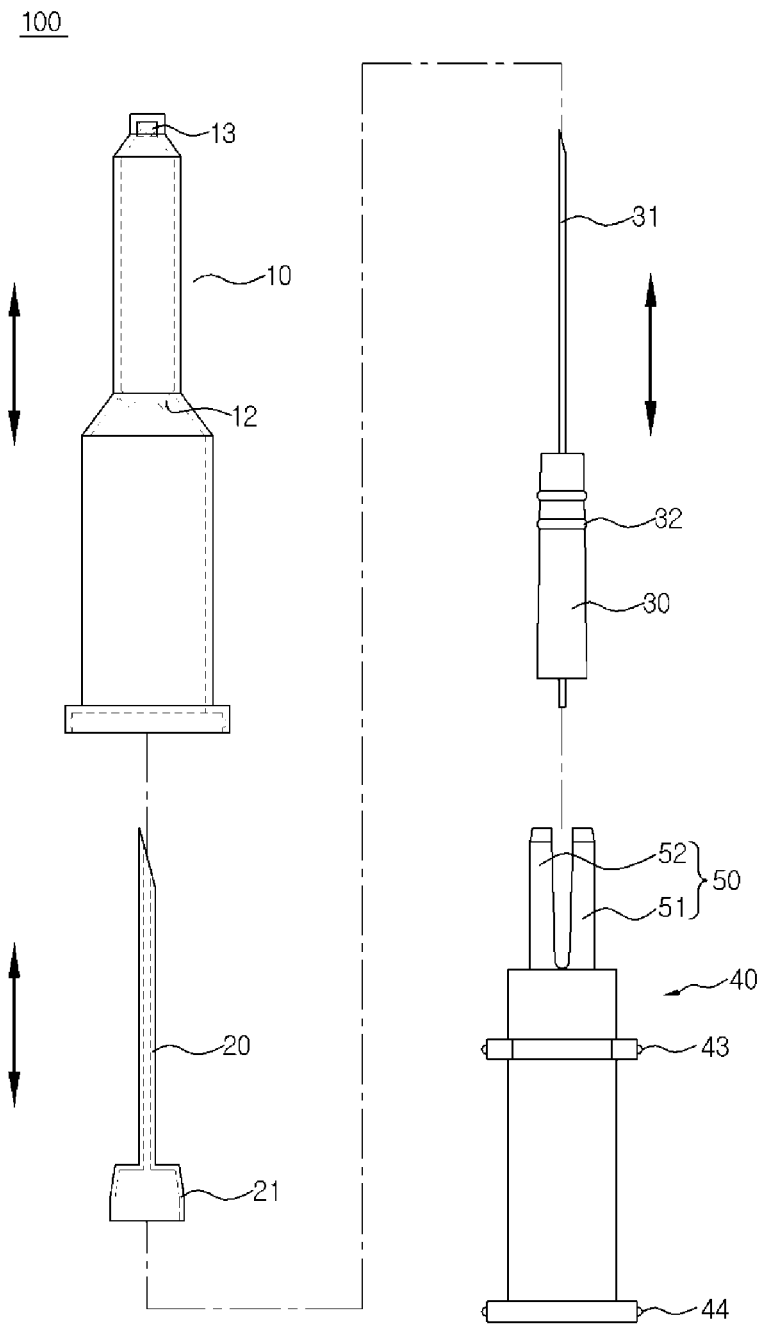
FIG. 10 is an exploded perspective view showing a fluid injection needle unit having a function of preventing needlestick injury and infection according to a second embodiment of the present invention.

Now, an explanation on the configuration and function of a fluid injection needle unit having a function of preventing needlestick injury and infection according to a second embodiment of the present invention will be in detail given with reference to the attached drawing. FIG. 10 is an exploded perspective view showing a fluid injection needle unit having a function of preventing needlestick injury and infection according to a second embodiment of the present invention, and FIG. 11 is a sectional view showing the fluid injection needle unit according to the second embodiment of the present invention.

Figure 11:
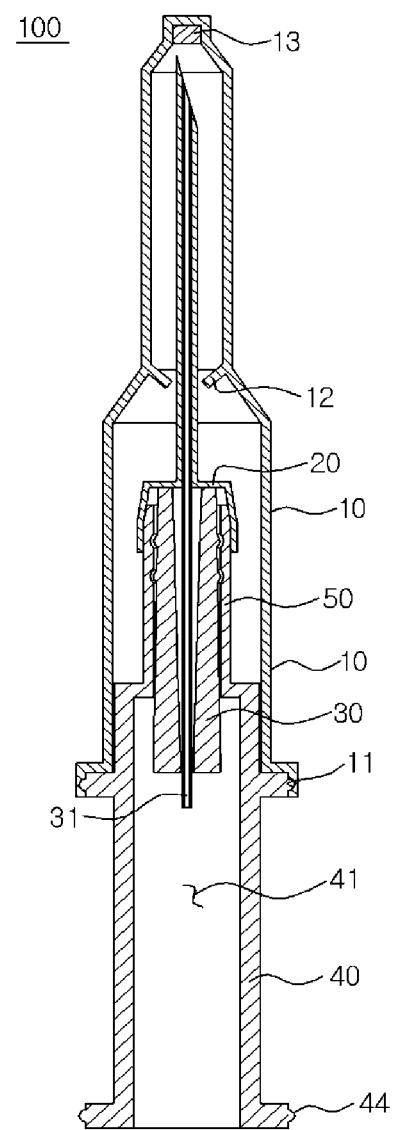
FIG. 11 is a sectional view showing the fluid injection needle unit according to the second embodiment of the present invention.

As shown in FIGS. 10 and 11, a fluid injection needle unit 100 having a function of preventing needlestick injury and infection according to the second embodiment of the present invention includes a cover 10, a needle film 20, a needle 31, a needle body 30, and a body 40, like the fluid injection needle unit 100 according to the first embodiment of the present invention.

According to the second embodiment of the present invention, the cover 10 is closed on top thereof and open on bottom thereof and has a hollow hole formed at the inside thereof, so that before the needle film 20 is inserted into a blood vessel of a patient, the needle film 20 and the needle 31 are accommodated into the hollow hole of the cover 10, thus preventing the occurrence of the needlestick injury and infection. After the needle film 20 is inserted into the blood vessel of the patient and thus detached from the needle unit 100, accordingly, the cover 10 is mounted onto a bottom end locking projection 44 of the body 40 as will be discussed later in the state of allowing the needle 31 and the needle body 30 to be accommodated thereinto, thus preventing the occurrence of the needlestick injury and infection.

According to the second embodiment of the present invention, further, the cover 10 includes an absorption layer 13 formed on the inner surface of the closed top end thereof so as to absorb the blood flowing when the needle film 20 is inserted into the blood vessel of the patient and to prevent the occurrence of infection. Furthermore, the cover 10 includes a deviation prevention barrier 12 formed along the inner intermediate periphery thereof so as to prevent the needle 31 and the needle body 30 from being deviated from the interior of the cover 10 when the needle 31 and the needle body 30 after used are inserted into the cover 10 so as to prevent the occurrence of the needlestick injury and infection.

As shown in FIGS. 10 and 11, the cover 10 has a mounting groove 11 formed along the inner bottom end periphery thereof, so that it is mounted onto a top end locking projection 43 formed along the outer top end periphery of the body 40. Before the needle film 20 is inserted into the blood vessel of the patient, further, the cover 10 is detached from the top end locking projection 43 of the body 40 and then mounted onto the bottom end locking projection 44 of the body 40.

According to the second embodiment of the present invention, further, the needle film 20 is configured to have the needle 31 inserted thereinto, like a general needle film, and after the needle 31 and the needle film 20 are inserted into the blood vessel of the patient, only the needle film 20 is detached from the needle unit 100. The needle film 20 has an expanded tube 21 formed on the lower end periphery thereof and an injection hole 22 formed along the interior thereof. According to the second embodiment of the present invention, as shown in FIG. 11, before the needle film 20 is inserted into the blood vessel of the patient, the expanded tube 21 is fitted to the outer peripheral surface of a tube-shaped insertion member 50 protruding upward from the top end portion of the body 40 and having incised portions 52, thus allowing the needle body 30 to be fixed to the body 40. After the needle film 20 has been inserted into the blood vessel of the patient, a fluid injection hose (not shown) is insertedly mounted into the expanded tube 21 of the needle film 20.

According to the second embodiment of the present invention, as shown in FIGS. 10 and 11, the needle body 30 has the needle 31 insertedly fixed to the upper end portion thereof and a mounting protrusion 32 formed along the outer peripheral surface thereof. The needle body 30 is desirably made of an elastic material. According to the second embodiment of the present invention, further, the needle body 30 is inserted into the insertion member 50 formed on the top end portion of the body 40 and fixedly mounted thereon by means of the expanded tube 21 of the needle film 20. Accordingly, if the expanded tube 21 is fitted to the outer peripheral surface of the insertion member 50 formed on top of the body 40, the needle body 30 is fixed to the insertion member 50 by means of a compression force of the insertion member 50, and if the needle film 20 is inserted into the blood vessel of the patient and detached from the needle unit 100, the compression force of the insertion member 50 is naturally released to allow the needle body 30 and the needle 31 to unitarily drop down into an insertion hole 41 of the body 40.

According to the second embodiment of the present invention, as shown in FIGS. 10 and 11, the body 40 has the top end locking projection 43 formed along the outer top end periphery thereof, the bottom end locking projection 44 formed along the outer bottom end periphery thereof, and the insertion hole 41 formed to pass through the interior thereof. In the state where the needle film 20 is kept before inserted into the blood vessel of the patient, accordingly, the mounting groove 11 of the cover 10 is fixedly mounted on the top end locking projection 43 of the body 40, and before the needle film 20 is inserted into the blood vessel of the patient, the cover 10 is detached from the top end locking projection 43 of the body 40 and fixed to the bottom end locking projection 44 thereof.

According to the second embodiment of the present invention, as shown in FIGS. 10 and 11, the insertion member 50 is formed on top of the body 40 and includes a plurality of holding portions 51 and the incised portions 52 formed between the holding portions 51.

Before the needle film 20 is detached from the needle unit 100, accordingly, if the expanded tube 21 is fitted to the outer peripheral surface of the insertion member 50, the insertion member 50 provides a given compression force to fix the needle body 30 thereto, and after the needle film 20 is inserted into the blood vessel of the patient and detached from the needle unit 100, the compression force of the insertion member 50 is released to allow the needle body 30 and the needle 31 to unitarily drop down into the body 40.

Next, an operating method of the fluid injection needle unit 100 having a function of preventing needlestick injury and infection according to the second embodiment of the present invention will be explained. As shown in FIG. 11, the needle body 30 is inserted into the insertion member 50 formed on top of the body 40 in the state where the needle film 20 is kept before inserted into the blood vessel of the patient, and the mounting groove 11 of the cover 10 is fixedly mounted on the top end locking projection 43 of the body 40 in the state where the needle film 20 is fitted to the needle 31, so that the needlestick injury and infection from the needle 31 and the needle film 20 can be prevented.

So as to allow the needle film 20 to be inserted into the blood vessel of the patient, first, the cover 10 is detached from the top end locking projection 43 of the body 40 and then fixed to the bottom end locking projection 44 thereof.

Figure 12:
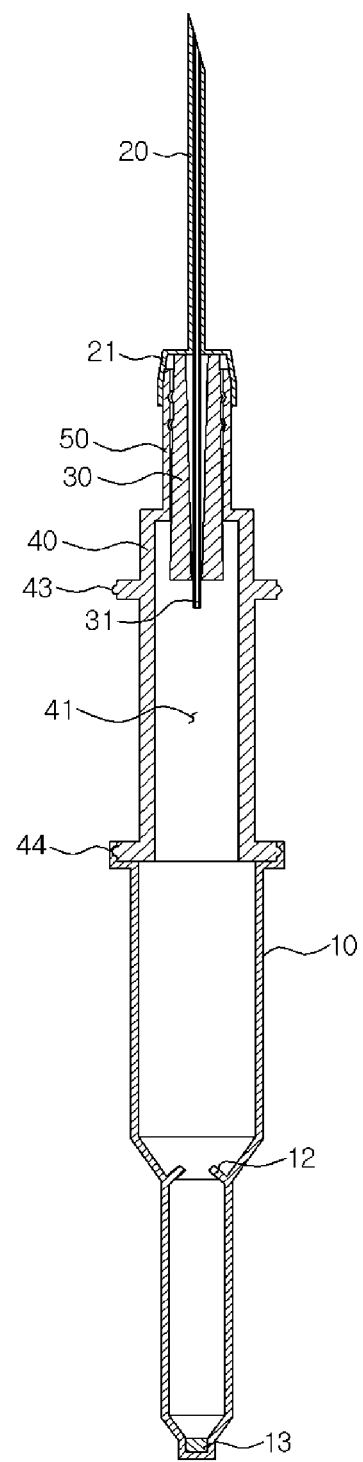
FIG. 12 is a sectional view showing the fluid injection needle unit according to the second embodiment of the present invention, wherein a cover is detached.

FIG. 12 is a sectional view showing the fluid injection needle unit according to the second embodiment of the present invention, wherein the cover 10 is detached from the top end locking projection 43 of the body 40 and then fixed to the bottom end locking projection 44 of the body 40.

So as to allow the needle film 20 of the fluid injection needle unit 100 according to the second embodiment of the present invention to be inserted into the blood vessel of the patient, as shown in FIG. 12, the cover 10, which is mounted onto the top end locking projection 43 of the body 40, is first detached therefrom and then fixed to the bottom end locking projection 44 of the body 40. Next, the needle 31 and the needle film 20 are inserted into the blood vessel of the patient, and after that, only the needle film 20 remains in the state of being inserted into the blood vessel of the patient, while the fluid injection needle unit 100 is pulling out from the blood vessel of the patient.

Figure 13:
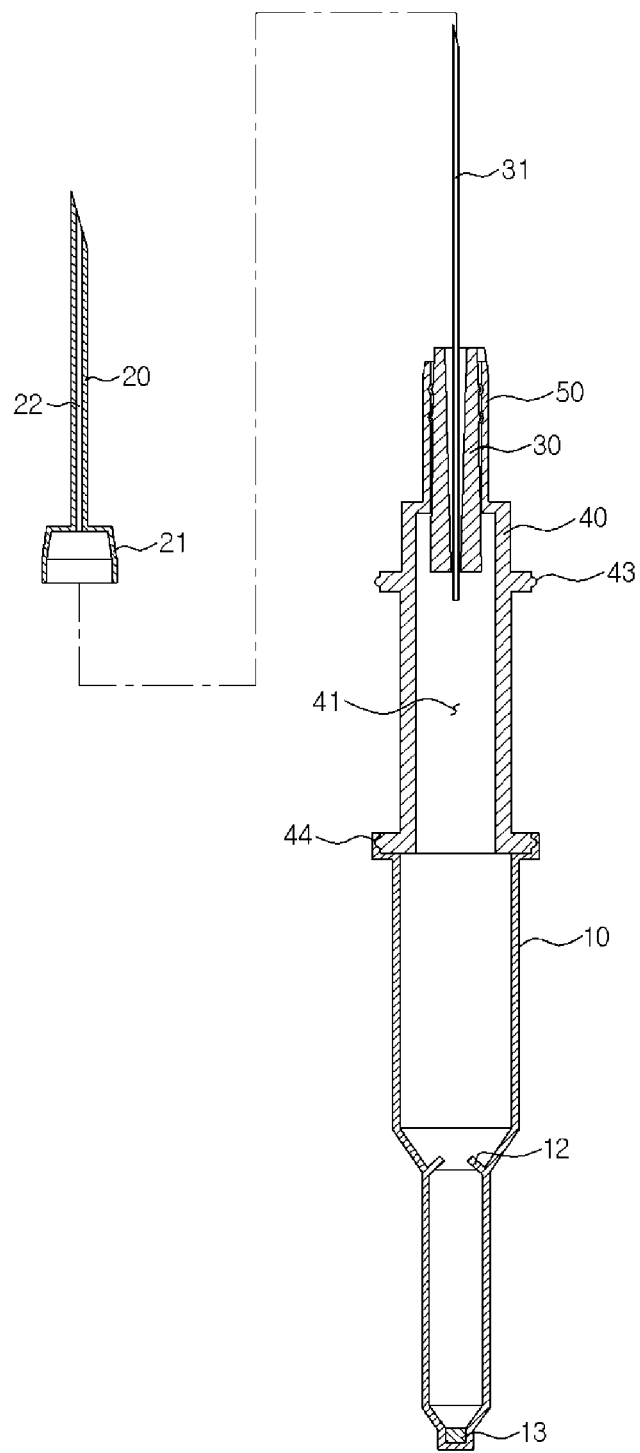
FIG. 13 is a sectional view showing the fluid injection needle unit according to the second embodiment of the present invention, wherein a needle film is detached.

FIG. 13 is a sectional view showing the fluid injection needle unit according to the second embodiment of the present invention, wherein the needle film 20 is detached. That is, FIG. 13 is a sectional view showing the fluid injection needle unit according to the second embodiment of the present invention, wherein the needle film 20 is inserted into the blood vessel of the patient and thus detached from the fluid injection needle unit 100.

According to the second embodiment of the present invention, after the needle film 20 is detached, the compression force of the insertion member 50 applied to the needle body 30 through the expanded tube 21 of the needle film becomes released.

Figure 14:
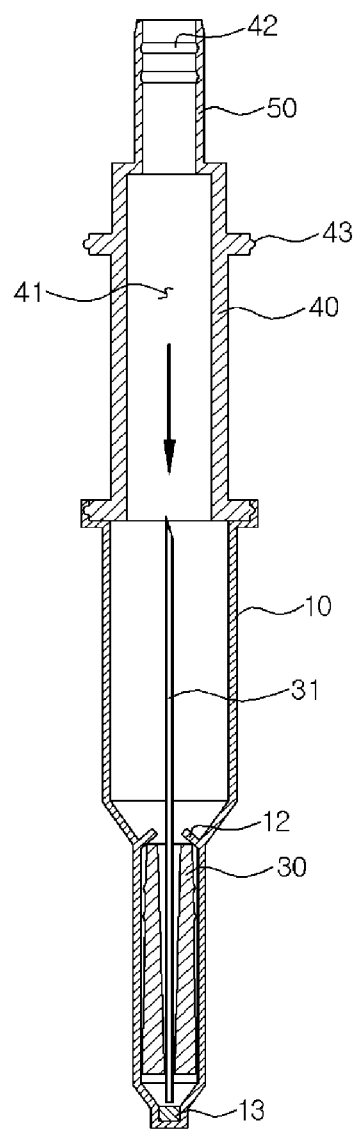
FIG. 14 is a sectional view showing the fluid injection needle unit according to the second embodiment of the present invention, wherein a needle and a needle body are inserted into a cover mounted on the bottom end periphery of a body.

FIG. 14 is a sectional view showing the fluid injection needle unit according to the second embodiment of the present invention, wherein the needle 31 and the needle body 30 are inserted into the cover 10 mounted on the bottom end periphery of the body 40.

According to the second embodiment of the present invention, as shown in FIG. 14, if the needle film 20 of the fluid injection needle unit 100 is inserted into the blood vessel of the patient, the needle film 20 is detached from the needle unit 100, and accordingly, the compression force of the insertion member 50 applied to the needle body 30 fixed to the inner peripheral surface of the insertion member 50 is naturally released to allow the needle body 30 and the needle 31 to unitarily drop down into the lower end portion of the body 40 and to then inserted into the cover 10.

After the fluid injection needle unit 100 is used, accordingly, the needle body 30 and the needle 31 are inserted into the cover 10 mounted on the bottom end periphery of the body 40, thus preventing the occurrence of the needlestick injury and infection.

As described above, the fluid injection needle unit having a function of preventing needlestick injury and infection according to the present invention is configured wherein the cover, the needle body and the body are improved in shape, and after the needle body is inserted into the blood vessel of the patient, the cover is coupled to the bottom end periphery of the body and the needle body is detached from the body by means of the detachable mounting members, so that the needle and the needle body are inserted unitarily into the cover to prevent the occurrence of the needlestick injury and infection.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A fluid injection needle unit having a function of preventing needlestick injury and infection, comprising:
    a needle film adapted to be inserted into a blood vessel of a patient and having an injection hole formed along an interior thereof;
    a body having an insertion hole formed to pass through a top and a bottom thereof, a top end locking projection formed along an outer top end periphery thereof, and a bottom end locking projection formed along an outer bottom end periphery thereof;
    a needle fixedly protruding from the top of the body in such a manner as to be inserted into the injection hole of the needle film before the needle film is inserted into the blood vessel of the patient;
    a cover having an internal space closed on top thereof and open on bottom thereof and configured to be fixedly mounted onto the top end locking projection of the body prior to the needle film being inserted into the blood vessel of the patient and further configured to be fixedly mounted onto the bottom end locking projection of the body after the needle film is inserted into the blood vessel of the patient;
    a needle body that is
        within the internal space of the cover and fixed to the insertion hole of the body by means of detachable mounting members when the cover is fixedly mounted onto the top end locking projections of the body and prior to the needle film being inserted into the blood vessel, and
        within the internal space of the cover and detached from the insertion hole of the body when the cover is fixedly mounted onto the bottom end locking projections of the body and after the needle film is inserted into the blood vessel of the patient.

2. The fluid injection needle unit according to claim 1, wherein the detachable mounting members comprise a mounting protrusion formed along an outer peripheral surface of the needle body and a locking groove formed along an inner peripheral surface of the insertion hole of the body.

3. A fluid injection needle unit having a function of preventing needlestick injury and infection, comprising:
    a needle film adapted to be inserted into a blood vessel of a patient and having an injection hole formed along an interior thereof;
    a body having an insertion hole formed to pass through a top and a bottom thereof, a top end locking projection formed along an outer top end periphery thereof, and a bottom end locking projection formed along an outer bottom end periphery thereof;
    a needle fixedly protruding from the top of the body in such a manner as to be inserted into the injection hole of the needle film before the needle film is inserted into the blood vessel of the patient;
    a cover having an internal space closed on top thereof and open on bottom thereof and configured to be directly mounted onto the top end locking projection of the body and not directly mounted onto the bottom end locking projection of the body prior to the needle film being inserted into the blood vessel of the patient, and further configured to be directly mounted onto the bottom end locking projection of the body and not directly mounted onto the top end locking projection of the body after the needle film is inserted into the blood vessel of the patient;

a needle body that is
- within the internal space of the cover and fixed to the insertion hole of the body by means of detachable mounting members when the cover is directly mounted onto the top end locking projections of the body and prior to the needle film being inserted into the blood vessel, and
- within the internal space of the cover and detached from the insertion hole of the body when the cover is directly mounted onto the bottom end locking projections of the body and after the needle film is inserted into the blood vessel of the patient.

\* \* \* \* \*